United States Patent [19]

Chambon et al.

[11] Patent Number: 6,093,873
[45] Date of Patent: Jul. 25, 2000

[54] GENETICALLY ENGINEERED MICE CONTAINING ALTERATIONS IN THE GENE ENCODING RXR

[75] Inventors: Pierre Chambon, Blaesheim; Philippe Kastner, Strasbourg, both of France

[73] Assignees: Institut National de la Santé et de la Recherche Médicale; Centre National de la Recherche Scientifique, both of Paris; Université Louis Pasteur, Strasbourg, all of France; Bristol-Myers Squibb Company, Princeton, N.J.

[21] Appl. No.: 08/914,256

[22] Filed: Aug. 19, 1997

Related U.S. Application Data

[60] Provisional application No. 60/024,175, Aug. 19, 1996.

[51] Int. Cl.$^7$ ............................ C12N 15/09; C12N 15/00; C12N 15/63; C12N 5/00
[52] U.S. Cl. .................................. 800/18; 800/3; 800/21; 800/22; 800/25; 435/455; 435/463; 435/462; 435/325; 435/320.1; 435/4
[58] Field of Search .................................. 800/18, 3, 21, 800/22, 25; 435/455, 463, 462, 325, 320.1, 4

[56] References Cited

U.S. PATENT DOCUMENTS 5,364,783  11/1994  Ruley et al. ........................... 435/235.1

FOREIGN PATENT DOCUMENTS

WO 94/26100  11/1994  WIPO.
WO 95/30741  11/1995  WIPO.

OTHER PUBLICATIONS

Moreadith et al., J. Mol. Med., vol. 75, pp. 208–216, 1997.
Capecchi, Scientific American, vol. 270, No. 3, pp. 34–41, Mar. 1994.
Westphal, FASEB J., vol. 3, pp. 117–120, 1989.
Accili, D., and Taylor, S.I., "Targeted inactivation of the insulin receptor gene in mouse 3T3–L1 fibroblasts via homologous recombination," *Proc. Natl. Acad. Sci. USA* 88:4708–4712 (1991).
Allenby, G., et al., "Retinoic acid receptors and retinoid X receptors: Interactions with endogenous retinoic acids," *Proc. Natl. Acad. Sci. USA* 90:30–34 (1993).
Bugge, T.H., et al., "RXRα, a promiscuous partner of retinoic acid and thyroid hormone receptors," *EBMO J.* 11:1409–1418 (1992).
Espeseth, A.S., et al., "Retinoic acid receptor expression vector inhibits differentiation of F9 embryonal carcinoma cells," *Genes & Dev.* 3:1647–1656 (1989).
Kliewer, S.A., et al., "Retinoid X receptor interacts with nuclear receptors in retinoic acid, thyroid hormone and vitamin $D_3$ signalling," *Nature* 355:446–449 (1992).
Mangelsdorf, D.J., et al., "Nuclear receptor that identifies a novel retinoic acid response pathway," *Nature* 345:224–229 (1990).

Marks, M.S., et al., "H–2RIIBP (RXRβ) heterodimerization provides a mechanism for combinatorial diversity in the regulation of retinoic acid and thyroid hormone responsive genes," *EMBO J.* 11:1419–1435 (1992).
Mullins, L.J., and Mullins, J.J., "Perspective Series: Molecular Medicine in Genetically Engineered Animals. Transgenesis in the Rat and Larger Mammals," *J. Clin. Invest.* 97:1557–1560 (Apr. 1996).
Nagpal, S., et al., "RARs and RXRs: evidence for two autonomous transactivation functions (AF–1 and AF–2) and heterodimerization in vivo," *EMBO J.* 12:2349–2360 (1993).
Sucov, H.M. et al., "RXRα mutant mice establish a genetic basis for vitamin a signaling in heart morphogenesis," *Genes & Dev.* 8 1007–1018 (1994).
Thomas, K.R., and Capecchi, M.R., "Site–Directed Mutagenesis by Gene Targeting in Mouse Embryo–Derived Stem Cells," *Cell* 51:503–512 (1987).
Zhang, X. –K., et al., "Retinoid X receptor is an auxiliary protein for thyroid hormone and retinoic acid receptors," *Nature* 355:441–446 (1992).
Bradley, D.J. et al., "Differential expression of α and β thyroid hormone receptor genes in rat brain and pituitary," *Proc. Natl. Acad. Sci. USA* 86:7250–7254 (1989).
Capecchi, M.R., "The New Mouse Genetics: Altering the Genome by Gene Targeting," *Trends in Genetics* 5(3):70–76 (1989).
Capecchi, M.R., "Altering the Genome by Homologous Recombination," *Science* 244:1288–1292 (1989).
Chambon, P., "The retinoid signaling pathway: molecular and genetic analyses," *Semin. Cell Biology* 5:115–125 (1994).
Dollé, P. et al., "Developmental expresion of murine retinoid X receptor (RXR) genes," *Mech. Devlop.* 45:91–104 (1994).
Green, S. "Promiscuous liaisons," *Nature* 361:590–591 (1993).
Hodgson, J., "Carbohydrate–Based Therapeutics," *Bio/Technology* 9:609–613 (1991).
Kastner, P. et al., "Genetic Analysis of RXRα Developmental Function: Convergence of RXR and RAR Signaling Pathways in Heart and Eye Morphogenesis," *Cell* 78:987–1003 (1994).

(List continued on next page.)

*Primary Examiner*—Bruce R. Campbell
*Assistant Examiner*—Jill D. Martin
*Attorney, Agent, or Firm*—Sterne, Kessler, Goldstein & Fox P.L.L.C.

[57] ABSTRACT

The present invention is directed to mice which are genetically altered to be deficient in the normal expression of RXRγ, to mice heterozygous for such deficiency, and to cell lines, preferably pluripotent or totipotent cell lines, which are heterozygous or homozygous for such deficiency. The invention further provides mice and cell lines which, in addition to being deficient in RXRγ, are genetically altered to be deficient in the expression of RXRα and/or RXRβ. The present invention further provides the use of any of the above mice and cell lines in situations where the absence of RXRγ, or the normal expression thereof, is desirable.

13 Claims, 9 Drawing Sheets

OTHER PUBLICATIONS

Kastner, P. et al., "Nonsteroid Nuclear Receptors: What Are Genetic Studies Telling Us about Their Role in Real Life?," *Cell* 83:859–869 (1995).

Kastner, P. et al., "Abnormal spermatogenesis in RXRβ mutant mice," *Genes & Dev.* 10:80–92 (Jan. 1996).

Liu, Q. and E. Linney, "The Mouse Retinoid–X Receptor–γ Gene: Genomic Organization and Evidence for Functional Isoforms," *Molecular Endocrinology* 7(5):651–658 (1993).

Luo, J. et al., "Compound mutants for retinoic acid receptor (RAR)β and RARα1 reveal developmental functions for multiple RARβ isoforms," *Mech. Devel.* 55:33–44 (Mar. 1996).

Mangelsdorf, D.J. et al., "Characterization of three RXR genes that mediate the action of 9–cis retinoic acid," *Genes & Devel.* 6:329–344 (1992).

Mangelsdorf, D.J. et al., "The RXR Heterodimers and Orphan Receptors," *Cell* 83:841–850 (1995).

Nagata, T. et al., "The mouse Rxrb gene encoding RXRβ: genomic organization and two mRNA isoforms generated by alternative splicing of transcrips initiated from CpG island promoters," *Gene* 142:183–189 (1994).

Sugawara, A. et al., "Isoform–Specific Retinoid–X Receptor (RXR) Antibodies Detect Differential Expression of RXR Proteins in the Pituitary Gland," *Endocrinology* 136(4):1766–1774 (1995).

Yu, V.C. et al., "RXRβ: A Coregulator That Enhances Binding of Retinoic Acid, Thyroid Hormone, and Vitamin D Receptors to Their Cognate Response Elements," *Cell* 67:1251–1266 (1991).

FIG.5A
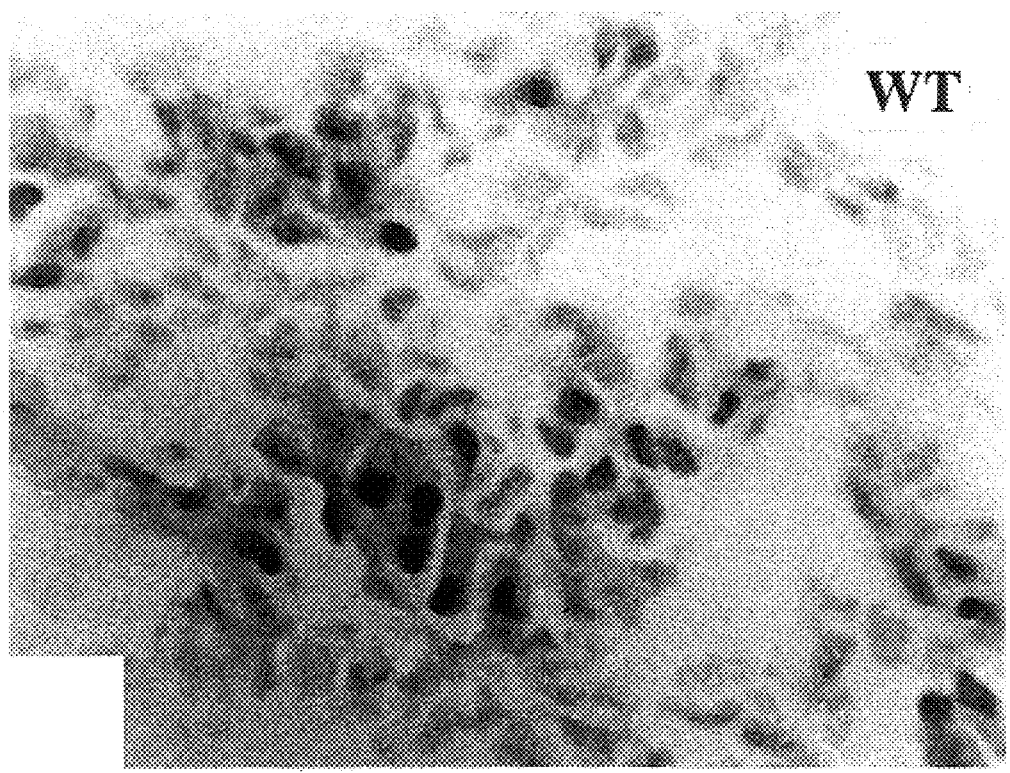
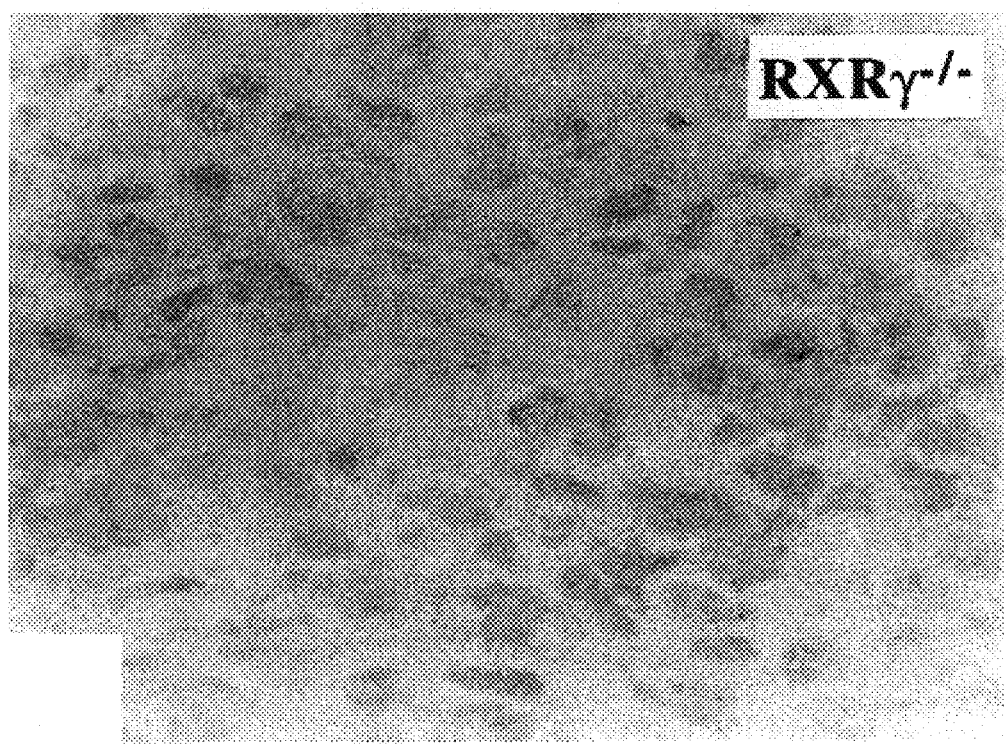
FIG.5B

GENETICALLY ENGINEERED MICE CONTAINING ALTERATIONS IN THE GENE ENCODING RXR

The present application claims benefit of the filing date of U.S. provisional application no. 60/024,175, filed Aug. 19, 1996, incorporated herein by reference.

BACKGROUND OF THE INVENTION

1. Field of the Invention

The present invention relates to the fields of retinoid X receptor γ (RXRγ) biology and transgenic mice. Specifically, the present invention relates to mice which are deficient in the normal expression of the gene encoding the RXRγ receptor, to mice heterozygous for such deficiency, to cell lines, preferably pluripotent or totipotent cell lines, which are heterozygous or homozygous for such deficiency, and to methods of using said mice or said cell lines to identify agonists and antagonists of the RXRγ receptor.

2. Description of the Related Art

Retinoids

A number of studies have demonstrated that retinoids (vitamin A derivatives) are essential for normal growth, vision, tissue homeostasis, reproduction and overall survival (for reviews and references, See Sporn et al., *The Retinoids*, Vols. 1 and 2, Sporn et al., eds., Academic Press, Orlando, Fla. (1984)). Retinoids are also apparently crucial during embryogenesis, since offspring of dams with vitamin A deficiency (VAD) exhibit a number of developmental defects (Wilson, J. G., et al., *Am. J. Anat.* 92:189–217 (1953)). With the exceptions of those on vision (Wald, G., et al., *Science* 162:230–239 (1968)) and spermatogenesis in mammals (van Pelt, H. M. M., and De Rooij, D. G., *Endocrinology* 128:697–704 (1991)), most of the effects generated by VAD in animals and their fetuses can be prevented and/or reversed by retinoic acid (RA) administration (Wilson, J. G., et al, *Am. J Anat.* 92:189–217 (1953); Thompson et al., *Proc. Royal Soc.* 159:510–535 (1964)). The dramatic teratogenic effects of maternal RA administration on mammalian embryos (Shenefelt, R. E., *Teratology* 5, 103–108 (1972); Kessel, M., *Development* 115:487–501 (1992); Creech Kraft, J., In *Retinoids in Normal Development and Teratogenesis*, G. M. Morriss-Kay, ed., Oxford University Press, Oxford, UK, pp.267–280 (1992)), and the marked effects of topical administration of retinoids on embryonic development of vertebrates and limb regeneration in amphibians (Mohanty-Hejmadi et al., *Nature* 355:352–353 (1992); Tabin, C. J., *Cell* 66:199–217 (1991)), have contributed to the notion that RA may have critical roles in morphogenesis and organogenesis.

Retinoid Receptors

Except for those involved in visual perception (Wald, G. et al., *Science* 162:230–239 (1968)), the molecular mechanisms underlying the highly diverse effects of retinoids have until recently remained obscure. The discovery of nuclear receptors for RA (Petkovich et al., *Nature* 330:444–450 (1987); Giguere et al., *Nature* 330:624–629 (1987)) has greatly advanced the understanding of how the retinoids may exert their pleiotropic effects (Leid et al., *TIBS* 1 7:427–433 (1992); Linney, E., *Current Topics in Dev. Biol.* 27:309–350 (1992)). It is thought that the effects of the RA signal are mediated through two families of receptors—the RAR family and the RXR family—which belong to the superfamily of ligand-inducible transcriptional regulatory factors that include steroid/thyroid hormone and vitamin D3 receptors (for reviews see Leid et al., *TIBS* 17:427–433 (1992); Chambon, P., *Semin. Cell Biol.* 5:115–125 (1994); Chambon, P., *FASEB J.* 10:940–954 (1996); Giguere, V., *Endocrinol. Rev.* 15:61–79 (1994); Mangelsdorf, D. J., and Evans, R. M., *Cell* 83:841–850 (1995); Gronemeyer, H., and Laudet, V., *Protein Profile* 2:1173–1236 (1995)).

RAR Receptors

Receptors belonging to the RAR family (RARα, β and γ and their isoforms) are activated by both all-trans- and 9-cis-RA (Leid et al., *TIBS* 17:427–433 (1992); Chambon, P., *Semin. Cell Biol.* 5:115–125 (1994); Dollé, P., et al., *Mech. Dev.* 45:91–104(1994)). Within a given species, the DNA binding (C) and the ligand binding (E) domains of the three RAR types are highly similar, whereas the C-terminal domain F and the middle domain D exhibit no or little similarity. The amino acid sequences of the three RAR types are also notably different in their B regions, and their main isoforms (α1 and α2, β1 to β4, and γ1 and γ2) further differ in their N-terminal A regions (Leid et al., *TIBS* 17:427–433 (1992)). Amino acid sequence comparisons have revealed that the interspecies conservation of a given RAR type is greater than the similarity found between the three RAR types within a given species (Leid et al., *TIBS* 17:427–433 (1992)). This interspecies conservation is particularly striking in the N-terminal A regions of the various RARα, β and γ isoforms, whose A region amino acid sequences are quite divergent. Taken together with the distinct spatio-temporal expression patterns observed for the transcripts of each RAR and RXR type in the developing embryo and in various adult mouse tissues (Zelent, A., et al., *Nature* 339:714–717 (1989); Dollé, P., et al., *Nature* 342:702–705 (1989); Dollé et al., *Development* 110:1133–1151 (1990); Ruberte et al., *Development* 108:213–222 (1990); Ruberte et al., *Development* 111:45–60 (1991); Mangelsdorfet al., *Genes & Dev.* 6:329–344 (1992)), this interspecies conservation has suggested that each RAR type (and isoform) may perform unique functions. This hypothesis is further supported by the finding that the various RAR isoforms contain two transcriptional activation functions (AFs) located in the N-terminal A/B region (AF-1) and in the C-terminal E region (AF-2), which can synergistically, and to some extent differentially, activate various RA-responsive promoters (Leid et al., *TIBS* 17:427–433 (1992); Nagpal, S., et al., *Cell* 70:1007–1019 (1992); Nagpal, S., et al., *EMBO J* 12:2349–2360 (1993)).

RXR Receptors

Unlike the RARs, members of the retinoid X receptor family (RXRα, β and γ) are activated exclusively by 9-cis-RA (Chambon, P., *Semin. Cell Biol.* 5:115–125 (1994); Dollé, P., et al., Mech. Dev. 45:91–104 (1994); Linney, E., *Current Topics in Dev. Biol.* 27:309–350 (1992); Leid et al., *TIBS* 17:427–433 (1992); Kastner et al., in *Vitamin A in Health and Disease*, R. Blomhoff, ed., Marcel Dekker, New York (1993)). However, the RXRs characterized to date are similar to the RARs in that the different RXR types also differ markedly in their N-terminal A/B regions (Leid et al., *TIBS* 17:427–433 (1992); Leid et al., *Cell* 68:377–395 (1992); Mangelsdorf et al., *Genes and Dev.* 6:329–344 (1992)), and contain the same transcriptional activation functions in their N-terminal A/B region and C-terminal E region (Leid et al., *TIBS* 17:427–433 (1992); Nagpal, S., et al., *Cell* 70:1007–1019 (1992); Nagpal, S., et al., *EMBO J* 12:2349–2360 (1993)).

It is currently unclear whether all the molecular properties of RXRs characterized in vitro are relevant for their physiological functions in vivo. In particular, it is unknown under what conditions these receptors act as 9-cis-RA-dependent transcriptional regulators (Chambon, P., *Semin. Cell Biol.* 5:115–125 (1994)). The knock-outs of RXRα and RXRβ in the mouse have provided some insight into the physiological functions of these receptors. For example, the ocular and cardiac malformations observed in RXRα$^{-/-}$ fetuses (Kastner, P., et al., *Cell* 78:987–1003 (1994); Sucov, H. M., et al., *Genes & Devel.* 8:1007–1018 (1994)) are similar to those found in the fetal VAD syndrome, thus suggesting an important function of RXRα in the transduction of a retinoid signal during development. The involvement of RXRs in retinoid signaling is further supported by studies of compound RXRα/RAR mutants, which reveal defects that are either absent or less severe in the single mutants (Kastner, P., et al., *Cell* 78:987–1003 (1994); Kastner, P., et al., *Cell* 83:859–869 (1995)). Moreover, it has been shown that activation of RA-responsive promoters likely occurs through RAR:RXR heterodimers rather than through homodimers (Yu, V. C. et al., *Cell* 67:1251–1266 (1991); Leid et al., *Cell* 68:377–395 (1992b); Durand et al., *Cell* 71:73–85 (1992); Nagpal et al., *Cell* 70:1007–1019 (1992); Zhang, X. K., et al., *Nature* 355, 441–446 (1992); Kliewer et al., *Nature* 355:446–449 (1992); Bugge et al., *EMBO J.* 11:1409–1418 (1992); Marks et al., *EMBO J.* 11:1419–1435 (1992); Yu, V. C. et al., *Cur. Op. Biotech.* 3:597–602 (1992); Leid et al., *TIBS* 17:427–433 (1992); Laudet and Stehelin, *Curr. Biol.* 2:293–295 (1992); Green, S., *Nature* 361:590–591 (1993)). These results strongly suggest that RAR/RXR heterodimers are indeed functional units that transduce the RA signal in vivo, although it is unclear whether all of the suggested heterodimeric combinations occur in vivo (Chambon, P., *Semin. Cell Biol.* 5:115–125 (1994)). Thus, the basis for the highly pleiotropic effect of retinoids may reside, at least in part, in the control of different subsets of retinoid-responsive promoters by cell-specifically expressed heterodimeric combinations of RAR-:RXR types (and isoforms), whose activity may be in turn regulated by cell-specific levels of all-trans- and 9-cis-RA (Leid et al., *TIBS* 17:427–433 (1992)).

The RXR receptors may also be involved in RA-independent signaling. For example, the observation of aberrant lipid metabolism in the Sertoli cells of RXRβ$^{-/-}$ mutant animals suggests that functional interactions may also occur between RXRβ and the peroxisomal proliferator-activated receptor signaling pathway (WO 94/26100; Kastner, P., et al., *Genes & Devel.* 10:80–92 (1996)).

RXRγ

While RXRα and RXRβ have a widespread (possibly ubiquitous) expression pattern during mouse development and in the adult animal (Mangelsdorf, D. J., et al., *Genes & Devel.* 6:329–344 (1992); Dollé, P., et al., *Mech. Devel.* 45:91–104 (1994); Nagata, T., et al., *Gene* 142:183–189 (1994)), RXRγ transcripts appear to have a more restricted distribution. In the embryo, RXRγ is mainly expressed in developing skeletal muscles where its expression persists throughout life. RXRγ is also expressed in the heart (after birth), sensory epithelia of the visual and auditory systems, specific structures of the central nervous system, and in tissues involved in thyroid hormone homeostasis, e.g., the thyroid gland and thyrotrope cells in the pituitary (Mangelsdorf, D. J., et al., *Genes & Devel.* 6:329–344 (1992); Dollé, P., et al., *Mech. Devel.* 45:91–104 (1994); Sugawara, A., et al., *Endocrinology* 136:1766–1774 (1995); Liu, Q., and Linney, E., *Mol. Endocrinol.* 7:651–658 (1993)).

It is yet unclear, however, whether this restricted expression of RXRγ corresponds to specific functions in vivo. To address this question, it would be of great importance to be able to establish a living model wherein the role of the RXRγ receptor could be studied in a definitive manner.

The mouse is the model of preference in the study of the mammalian genetic system, and a great deal of research has been performed to map the murine genome. Accordingly, it is an object of the present invention to generate strains of mice which do not express, or express at undetectable levels, the RXRγ receptor. Such mice would be of great value for a better understanding of the role of RXRγ because such animals, and cell lines leading to or derived from such animals, would allow direct testing of the function of specific genes, either deleted or reintroduced by transgenesis, and would serve as an assay system to identify compounds which act as antagonists or agonists of the RXRγ receptor.

SUMMARY OF THE INVENTION

The present invention describes the generation of transgenic mice, produced via homologous recombination in embryonic stem (ES) cells, in which RXRγ has been functionally inactivated. This invention thereby provides an animal model useful in studies designed to elucidate the functional role of RXRγ in vivo during mouse development and post-natal life Specifically, the present invention provides mice and mouse cell lines which are deficient in the normal expression (either incapable of total or detectable functional expression) of RXRγ. More specifically, the present invention describes mice and cell lines which have been genetically altered such that the normal expression of the gene encoding RXRγ has been disrupted such that it no longer encodes functional or detectable levels of the RXRγ receptor.

The invention further provides mice and cell lines which are heterozygous for the above deficiency.

The invention also provides mice and cell lines which, in addition to being genetically altered such that the expression of RXRγ is disrupted, are genetically altered such that expression of RXRα and/or RXRβ is also disrupted.

Utilizing one or more of the aforementioned mice or cell lines, the present invention further provides methods of identifying antagonists and agonists of RXRγ. Specifically, the isoform of RXRγ specific for a given agent, and the effects the agent has on inducing retinoid-dependent gene expression, can be assayed by first incubating an agent with a cell line, a transgenic mouse, or cells or tissues derived therefrom, which is deficient in the normal expression of one or more isoforms of RXRγ, determining the amount of agent bound or determining the level of retinoid-dependent gene expression which is induced in the cell lines or specific tissues of the transgenic mice, and then comparing the amount of agent bound by, or level of gene expression induced in, the genetically altered cell lines, tissues or mice to those of cell lines, tissues or mice that have not been genetically altered to be deficient in RXRγ receptor expression.

BRIEF DESCRIPTION OF THE FIGURES

FIGS. 5A–B. Absence of RXRγ1 protein in muscles of mutant mice. (A) Immunohistochemical nuclear staining of RXRγ1 in myoblast cells of wild type (WT) intercostal muscle in a 14.5 days-post-coitus (dpc) fetus. (B) no signal was detected in the corresponding muscle of a 14.5 dpc RXRγ$^{-/-}$ fetus. Magnification ×200.

DETAILED DESCRIPTION OF THE INVENTION

Figure 1:
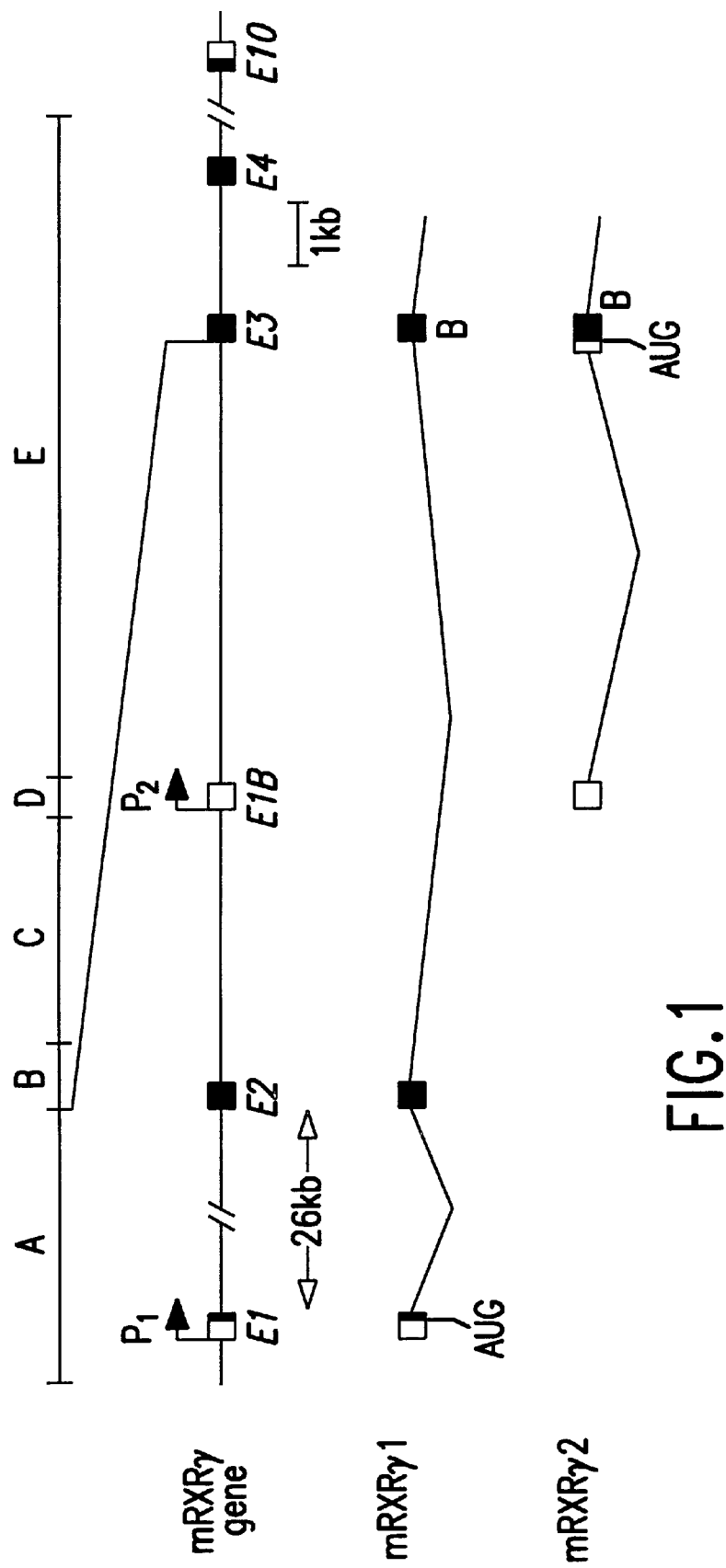
FIG. 1. Disruption of mouse RXRγ (mRXRγ) gene. Schematic representation of the A–F regions of the RXRγ receptor and of the RXRγ 5' region together with the alternatively spliced mRXRγ1 and mRXRγ2 transcripts. Exons containing coding (filled boxes) and non-coding (open boxes) sequences were numbered as in Liu & Linney (Liu, Q. & Linney, E., *Mol. Endocrinol.* 7:651–658 (1993)).

The present invention provides; 1) mice which are deficient in expressing either functional, normal levels, or detectable levels of one or more isoforms of the RXRγ receptor; 2) mice heterozygous for such a deficiency; 3) mice which, in addition to being deficient in expressing RXRγ, are also deficient in expression of either functional, normal levels, or detectable levels of one or more isoforms of the RXRα and/or the RXRβ receptors; 4) cell lines, preferably pluripotent or totipotent cell lines, which are heterozygous or homozygous for such deficiency; and 5) methods of using the cell lines and mice of the present invention, or tissues derived therefrom, to identify antagonists and agonists of RXRγ.

The present invention uses the technique of homologous recombination, as disclosed in WO 94/26100 (which is incorporated by reference herein in its entirety), to replace one or more of the sequences encoding RXRγ with a sequence which either prevents expression of all of the isoforms, or of a specific isoform, of RXRγ, or with a sequence which encodes an altered form of the receptor. It has previously been demonstrated that gene replacement techniques can be used to knock out or alter the expression of RXRα and the RAR family of receptors (See WO 94/26100).

In one embodiment, the present invention provides mice and cell lines which have been altered to contain a sequence which confers a deficiency in the normal expression of at least one isoform of RXRγ. The cell lines and mice of the present invention can be heterozygous or homozygous for the desired trait, provided that the mice or cell lines contain the altered RXRγ coding sequence.

As used herein, a mouse or cell line is said to be genetically altered to contain a sequence which conveys a deficiency in the normal expression of RXRγ if recombinant techniques are utilized to insert, delete, replace or otherwise disrupt sequences encoding, or directing the expression of, one or more isoforms of RXRγ. The insertion, deletion, replacement or disruption within such sequences has the effect of altering the normal level of expression of the given sequence or altering the activity of the protein which is expressed.

Mice can be altered such that the mouse expresses a lower level of the protein when compared to a non-altered mouse. In some instances, where a mouse is altered such that a target gene is deleted or a large exogenous DNA sequence is inserted within the target sequence, the mouse will not produce detectable levels of the given receptor. However, in some instances it may be possible for extremely low quantities of the given receptor to be produced, although such product may, in itself, be inoperative or nonfunctional in its usual physiological actions.

As used herein, "wild-type" refers to an animal or cell line that has not been genetically altered.

As used herein, "normal expression" is defined as the level of expression which is present in a wild-type animal or cell line. Accordingly, as used herein a mouse or cell line is said to be "deficient in normal expression" if the mouse or cell line expresses lower levels (including the total absence thereof) of a functional RXRγ receptor when compared to that which is present in a wild-type animal or cell line. A variety of techniques known in the art can be used to quantitate the level at which a given protein is expressed. These include, but are not limited to immunological techniques such as ELISA, RIA, western blot or flow cytometry/FACS, or quantitative analytical techniques such as spectroscopy or chromatographic methods including HPLC, FPLC, affinity or flame chromatography.

Alternatively the mice of the present invention can be altered so as to express an altered form of the given protein. Mice can be altered such that a specific mutation is introduced into a given region of a specific isoform of RXRγ. Alternatively, mice can be altered such that the specific isoform of RXRγ is altered (for example, the sequence encoding RXRγ1 can be replaced with sequence encoding RXRγ2) and the subsequent effects observed.

As used herein, the RXRγ subtype of receptors is defined as proteins which share the overall structure and sequence organization of members of the nuclear receptor proteins thus far identified as RXRγ receptors. These include, but are not limited to, all the various isoforms of RXRγ, for example the RXRγ1 and RXRγ2 isoforms disclosed in Liu, Q., and Linney, E., *Mol. Endocrinol.* 7:651–658 (1993), which is herein incorporated by reference.

As used herein, a "subtype" of an RXR receptor is identified by the presence of a subtype specific sequence which occurs within the A, B, D and/or regions of the receptor. All isoforms from a given organism of a specific RXR subtype, for example all isoforms of human RXRγ, possess a conserved sequence within one of these regions which defines the subtype.

As used herein, an "isoform" of RXRγ is identified by sequence heterogeneity which is present in the A region of the RXRγ receptor. The various isoforms of RXRγ (e.g., RXRγ1, RXRγ2) from a given organism will possess differing A region sequences.

Using the procedures outlined in the Examples presented below as well as those known in the art, in particular those disclosed in WO 94/26100, one of ordinary skill can generate vectors for altering the expression of one or more specific isoforms of RXRγ without undue experimentation. Specifically, an individual wishing to use homologous recombination (HR) to disrupt a specific isoform of RXRγ first uses the sequences encoding one of the various isoforms of RXRγ disclosed in Liu, Q., and Linney, E., *Mol. Endocrinol.* 7:651–658 (1993), to isolate a genomic fragment encoding a region of the receptor of interest, modifies a certain portion of the genomic fragment to create a null allele for the receptor, and then uses this modified genomic sequence to perform HR. For example, Example 1 describes vectors which selectively inactivate the entire RXRγ subtype (these vectors contain a deletion of sequences of the B and C regions of RXRγ). Specifically, the replacement of the endogenous sequence by an exogenous DNA sequence (including, e.g., a marker gene sequence such as Neo), thus removing or disrupting one or more of the exons of a RXRγ receptor (see FIG. 1), will disrupt the expression of the RXRγ gene such that mice carrying such (an) insertion(s) in their somatic cells will be deficient in the normal expression of a RXRγ receptor. In the same way, mice carrying such (an) insertion(s) in their germ line cells will pass this mutation on to their progeny (with predicted Mendelian inheritance patterns) such that the progeny will be heterozygous or homozygous (if the parents are both heterozygous) for the deficiency in the normal expression of the RXRγ receptor. In principle, similar disruptions in the normal expression of a RXRγ receptor may be expected to result from alteration (via insertions or deletions as in the present strategy) of any of exons E1 to E10 of RXRγ (see FIG. 1), so as to obtain total, or isoform-specific (for alterations made in the E1 and E2 exons) RXRγ receptor mutants.

The mice and cell lines of the present invention are preferably obtained by a method known in the art as homologous recombination (HR). This method has long been known in lower eukaryotes (e.g., yeast), and has also been described for the mouse (for review, see Capecchi, M., *Trends Gen.* 5(3):70–76 (1989)). HR has also proven useful for the construction of mice and cell lines that are genetically altered with respect to expression of various subtypes and isoforms of RAR receptors and isoforms of RXRα (WO 94/26100).

HR essentially comprises isolating genomic sequences containing the target gene, employing known genetic engineering techniques to mutate or otherwise disable (i.e., "knock out") or modify the gene, and then reintroducing the gene into the relevant species. This is achieved by preparing a culture of pluripotent, or totipotent, cells, typically taken from animal embryos (embryonic stem or "ES" cells). The advantage of ES cells is that they can be successfully cultured for a large number of generations under conditions in which they will not differentiate, allowing the introduction of exogenous DNA into somatic and/or germline cells of embryonic animals. Following introduction of the foreign DNA, the ES cells are removed from their differentiation block and then can be reintroduced into recipient embryos, where they differentiate into mature somatic or germline cells carrying the exogenous DNA (or "transgene").

A variety of methods may be used to introduce foreign DNA into recipient cells, including calcium phosphate precipitation, microinjection, lipofection, viral transduction or electroporation. In carrying out the present invention, the technique of electroporation is typically used to render the ES cells capable of taking up exogenous DNA. The modified gene is then introduced, in a suitable manner, to these cells. Once taken up, the exogenous DNA is often incorporated into the genome of the recipient cells via non-homologous recombination (random integration), although incorporation may alternatively proceed by homologous recombination.

To select cells in which a recombination event has taken place, a selectable marker sequence, many of which are well-known in the art, may be used. For example, the use of the bacterial Neo gene to confer resistance to neomycin, or an analogue thereof such as G418, is routine. The marker gene may be inserted in the gene to be modified, thereby disabling the target gene, while providing a positive selectable marker. Clones which are Neo$^+$ (i.e., which are resistant to neomycin and therefore capable of growth in neomycin- or G418-containing media) have integrated the vector by homologous or non-homologous recombination.

To select for homologous recombinants, the ends of the modified gene may have other markers inserted, such as the Herpes Simplex Virus thymidine kinase (HSVTK) gene. In a HR event, only those sequences homologous to the target gene will be recombined; thus, the HSVTK genes will not be recombined, and the marker will not be transferred into the target sequence. Therefore, the desired homologous recombinant will be resistant to, for example, gancyclovir, which is converted into a toxic metabolite when the HSVTK gene product is present (as would occur following a non-homologous recombination event).

Correct clones may be identified by the techniques of PCR or by genomic Southern blotting, which are routine to those of ordinary skill in the art. When a suitable clone has been identified, the ES cells may be injected into early-stage embryos (blastocysts) and reintroduced into a pseudopregnant female. Chimeric animals will generally result from at least some of these reimplanted embryos, their tissues deriving in part from the selected clone. In these animals, in addition to the somatic cells the germline cells (spermatozoa or ova) may also be chimeric, containing the modified gene. Progeny deriving from such germ cells will be heterozygous for the gene or will revert to the wild type, following the expected Mendelian inheritance frequencies.

The heterozygous progeny can be cross-bred to yield homozygous animals, which should also occur with predicted Mendelian inheritance. Confirmation of the allelic structure of the mice (i.e., heterozygous, homozygous or wild type) can be ascertained by a variety of routine methods, e.g., Southern blotting.

The mice and cell lines of the present invention may also be deficient in the expression of other genes, and thus provide the opportunity to study the interactions of RXRγ proteins with other proteins, or the effects these proteins have on retinoid-dependent gene expression. For example, in addition to animals deficient in RXRγ, the present invention provides mice that are further deficient in one or more additional RXR subtypes. To this end, an RXRγ mutation can be introduced onto RXRα and/or RXRβ mutant genetic backgrounds as described in Example 3. Furthermore, using these same methods animals or cell lines may be created which comprise combinations of mutations affecting RXRγ together with mutations of either RARβ, thyroid hormone receptor a or thyroid hormone receptor β. These latter combinations may be of particular interest since these genes are co-expressed with RXRγ in a number of tissues (Dollé, P., et al., *Mech. Dev.* 45:91–104 (1994); Bradley, D. J., et al., *Proc. Natl. Acad. Sci. USA* 86:7250–7254 (1989)).

The present invention also envisages cell lines suitable for generating mice of the invention, and techniques for generating such lines and mice.

Thus, to obtain mice according to the present invention, one skilled in the art can use the strategy of homologous recombination (HR) in embryonic stem cells (ES cells) to replace the wild-type sequences encoding one or more isoforms of RXRγ with an altered sequence.

The absence of one or more isoforms of RXRγ in a cell line or animal allows one skilled in the art to screen for genes and agents which can restore the altered mice to a wild-type phenotype, as well as to screen for agents which act as agonists or antagonists of one or more isoforms of RXRγ, using methods described for similar studies of the RAR family of receptors and for RXRβ (WO 94/26100).

The mice and cell lines of the present invention allow the investigation, at the cellular level as well as at the in vivo level, of a system which lacks one or more specific isoforms of RXRγ. This capability will allow the establishment of the importance of each of RXRγ, and its various isoforms, in animal development and physiology.

Thus, it will be appreciated that there are many uses to which the mice and cell lines of the present invention may be put. They are particularly useful in studying any aspect of RA mediated gene expression and tissue specific expression of various RXRγ receptors. In addition, the mice and cell lines of the present invention may be used to identify agonists and antagonists of specific members of the RAR/RXR class of receptors using methods described previously (WO 94/26100).

To assay an agent for its possible agonistic or antagonistic activity, in general the agent which is to be tested will be incubated with one or more of the cell lines or mice of the present invention or tissues derived therefrom. The level of binding of the agent is then determined, or the effect the agent has on development or gene expression is monitored, by techniques that are routine to those of ordinary skill.

As used herein, the term "incubate" is defined as contacting the compound or agent under investigation with the appropriate cell or tissue of the invention, or administering the agent or compound to the appropriate mouse of the invention via any one of the well-known routes of administration including enteral, intravenous, subcutaneous, and intramuscular.

For example, the cell lines and mice of the present invention, or tissues derived therefrom, can be used in an assay system comprising the steps of: (a) incubating an agent with one or more of the cell lines or mice of the present invention, or cells or tissues derived therefrom; (b) determining whether the agent binds to the cells, tissues, or mice, or determining the effects the agent has on development or gene expression; and (c) comparing the binding of the agent to, or the effects of the agent on, the cells, tissues or mice of the present invention to the binding of the agent to, and/or effects of the agent on, cells, tissues or mice that express normal levels of a functional RXRγ receptor.

In performing such an assay, one skilled in the art will be able to determine which isoform of RXRγ an agent binds to, and hence determine what specific receptor(s) are utilized by a given compound. Additionally, one can determine in which tissues a given RXRγ receptor is active.

The agents screened in the above assay can be, but are not limited to, peptides, carbohydrates, steroids and vitamin derivatives. The agent can be selected and screened at random, or can be rationally selected or rationally designed using protein modeling techniques.

For random screening, agents such as peptides, carbohydrates, steroids or vitamin derivatives (e.g., derivatives of RA) are selected at random and are assayed, using direct or indirect methods that are routine in the art, for their ability to bind to RXRγ or a functional retinoid receptor heterodimer comprising RXRγ that is present in mice or cell lines described in the present invention.

Alternatively, agents may be rationally selected. As used herein, an agent is said to be "rationally selected" when the agent is chosen based on the physical structure of a known ligand of RXRγ or a functional heterodimeric retinoid receptor comprising RXRγ. For example, assaying compounds possessing a retinol-like structure would be considered a rational selection since retinol-like compounds are known to bind to a variety of retinoid receptor heterodimers.

Since highly purified RAR and RXR proteins are now available, X-ray crystallography and NMR-imaging techniques can be used to identify the structure of the ligand binding site present on these proteins and, by extension, that which is specifically present on one or more RXRγ isoforms. Utilizing such information, computer modeling systems are now available that allows one to "rationally design" an agent capable of binding to such a defined structure (Hodgson, *Biotechnology* 8:1245–1247 (1990)), Hodgson, *Biotechnology* 9:609–613 (1991)).

As used herein, an agent is said to be "rationally designed" if it is selected based on a computer model of the ligand binding site of one or more RXRγ isoforms.

In one aspect of the above-described assay, the cell line or mouse, in addition to being altered in the expression of one or more isoforms of RXRγ, is altered such that it contains a marker sequence such as luciferase, beta galactosidase, green fluorescent protein or chloramphenicol acyltransferase, operably linked to a RXRγ response element (RXRγRE). The agent which is to be tested is incubated with the altered cell or mouse, or tissues derived therefrom, and the expression of the reporter sequence is assayed. In this fashion, agents can be identified which are capable of either stimulating or inhibiting the expression of a DNA sequence which is controlled by a specific RXRγRE.

The following Examples serve only to illustrate the invention, and are not to be construed as in any way limiting on the invention.

EXAMPLES

Example 1

Genomic Organization and Disruption of the RXRγ Gene

Experimental Procedures

Construction of RXRγ Targeting Vectors.

Figure 3:
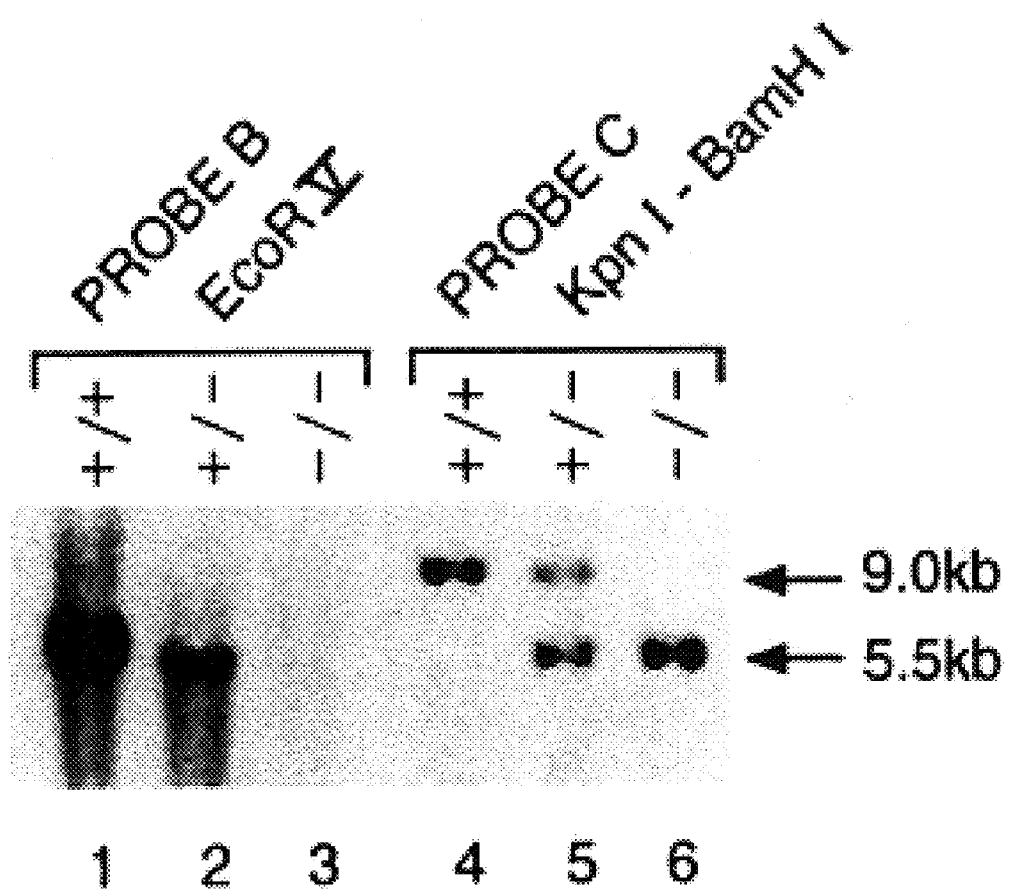
FIG. 3. Disruption of mRXRγ gene. Characterization of targeted ES cells. Southern analysis of KpnI-restricted DNA from YJ3, YJ36 and wild type (D3) ES cell clones with probes A and C.
Figure 4:
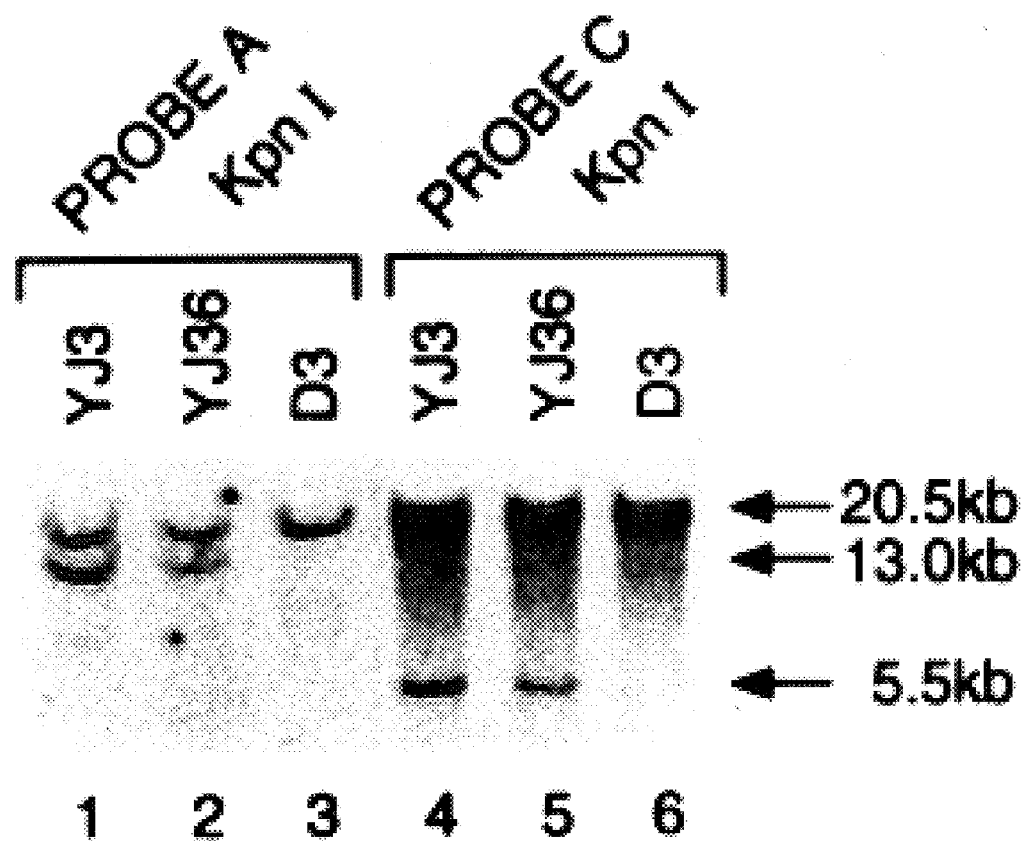
FIG. 4. Disruption of mRXRγ gene. Southern blot analysis of mutant mice. Lanes 1–3: the absence of the deleted fragment in the RXRγ$^{-/-}$ genome was checked by hybridization of EcoRV restricted DNA with probe B. Lanes 4–6: an example of routine genotyping of RXRγ mutant mice.

RXRγ genomic clones (FIGS. 1 and 2) were obtained by screening an ES-cell derived genomic library (ESγ GEM 12) with a mRXRγ full length cDNA probe. To construct the targeting vector (FIG. 2), the 2.5 kb SacI-EcoRI genomic fragment was first subcloned into a PGK-NEO poly(A)+ cassette (derived from pKJ-I; Adra, C. N., et al., *Gene* 60:65–74 (1987)) on the 3' side of the neomycin resistance gene. Subsequently, the 5.5 kb XbaI genomic fragment was inserted 5' to the NEO cassette. Thus in the resulting plasmid, the NEO sequences replace a 2.5 kb XbaI-SacI RXRγ genomic fragment containing exons 3 and 4, which encode the entire DNA-binding domain (see FIG. 2). The final targeting vector was obtained by insertion of a GTI.II-tk cassette (Lufkin, T., et al., *Cell* 66:1105–119 (1991)) at the 3' end of the construct, linearized with XhoI, and was electroporated into D3 ES cells. G418- and gancyclovir-selection, genomic DNA extraction, Southern blotting and generation of chimeras were as described (Luflin, T., et al., *Cell* 66:1105–119 (1991)). To identify homologous recombination (HR) events, KpnI-restricted DNA was analyzed by Southern blot with probes A or C (FIGS. 2 and 3) and with a neomycin probe (data not shown). Probe B (a 1.5 kb long XbaI-MscI genomic fragment) was further used to analyze the targeted locus after EcoRV digestion (FIG. 4).

Results

Characterization of RXRγ genomic clones.

As a first step in constructing a targeting vector to disrupt the RXRγ gene, RXRγ genomic clones were isolated and characterized. These studies revealed that the 5' region of the RXRγ gene is very large and spans over 35 kb (FIG. 1), resembling in that respect the RXRα gene (Broccard, J., and Kastner, P., unpublished results), but not the RXRβ gene which is very compact (Nagata, T., et al., *Gene* 142:183–189 (1994). It was also found that, in contrast to what was reported by Liu and Linney (Liu, Q. & Linney, E., *Mol. Endocrinol.* 7:651–658 (1993)), the second RXRγ1-specific exon (E2) is located upstream of the RXRγ2-specific 5' exon (E1B, FIG. 1). The RXRγ gene organization determined in the current studies was otherwise identical to that reported by Liu and Linney.

Homologous recombination and germ line transmission of RXRγ gene.

Figure 2:
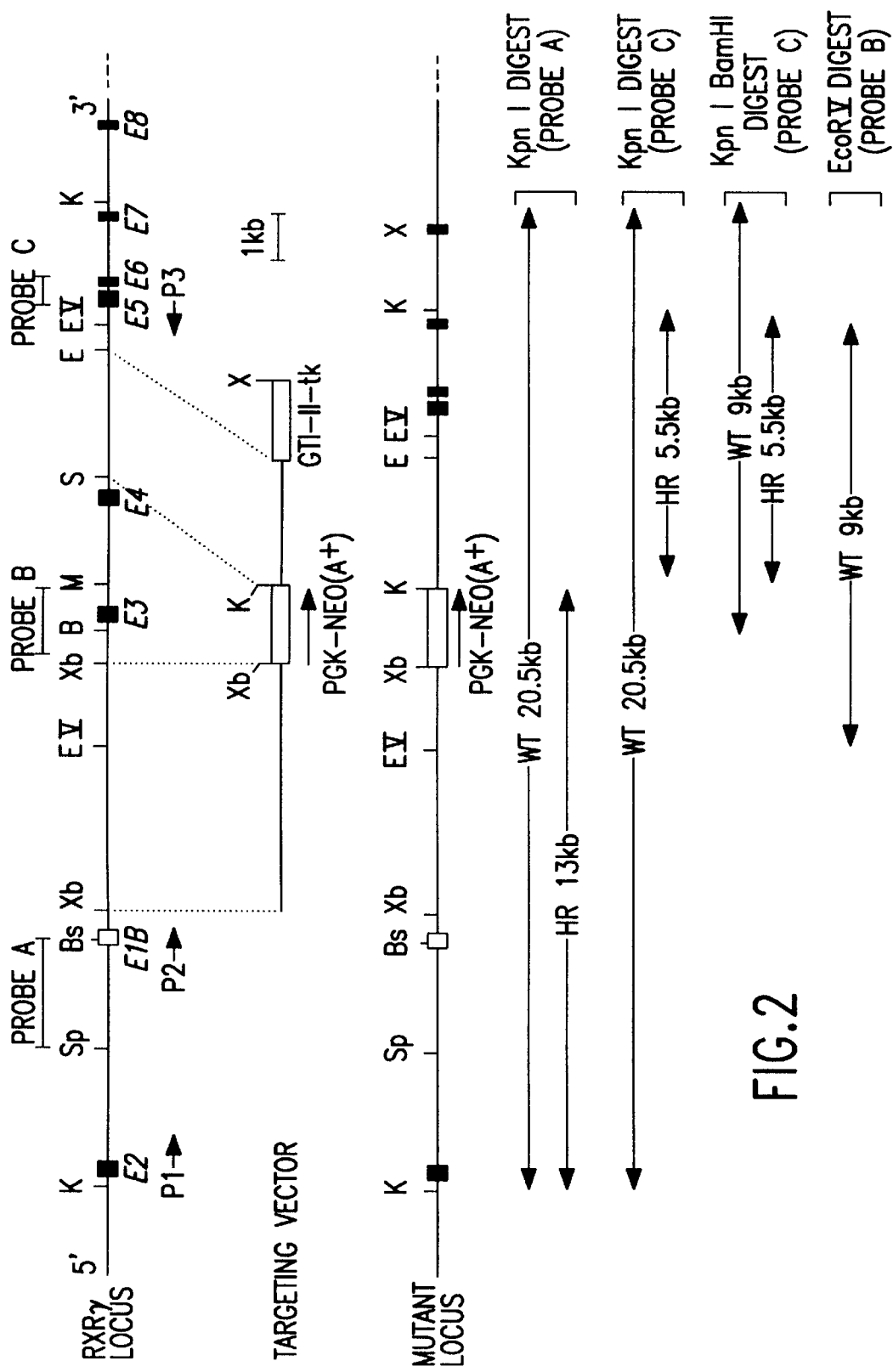
FIG. 2. Disruption of mRXRγ gene. Schematic genomic map of the RXRγ gene, as well as of the targeting vector and structure of the mutant locus. Probe A is a 2.5 kb SpeI-BspEI fragment, probe B is a 1.5 kb XbaI-MscI fragment, probe C is a 400 base pair-long PCR fragment spanning the region between exons E5 and E6. Restriction sites: (B) BamHI; (Bs) BspEI; (E) EcoRI; (EV) EcoRV; (K) KpnI; (M) MscI; (S) SacI; (Sp) SpeI; (Xb) XbaI; (X) XhoI.

A replacement-type targeting vector (Capecchi, M. R., *Science* 244:1288–1292 (1989)) was constructed by replacing a 2.5 kb XbaI-SacI fragment, which contains the third and the fourth exons encoding the RXRγ DNA-binding domain (Liu, Q., and Linney, E., *Mol. Endocrinol.* 7:651–658 (1993)), with a PGK-NEO-poly(A)+ cassette (FIG. 2). Six targeted clones were obtained after electroporation into D3 ES cells and selection with G418 and gancyclovir. Homologous recombination was confirmed by Southern analysis using probes A and C (FIG. 2). Upon further analysis with a "neomycin" probe, two clones exhibited additional integration events (data not shown). The remaining four clones were injected into C57BL/6 blastocysts to produce chimeras. Germline transmission was obtained from chimeras derived from two of these clones (YJ3 and YJ36).

Example 2

Analysis of RXRγ Mutant Mice

Experimental Procedures

Generation of homozygous and heterozygous mutant mice.

Heterozygous mutant mice (RXRγ$^{+/-}$), including chimeras demonstrating germline transmission, were prepared by genetic manipulation of C57BL/6 blastocysts as described for Example 1. Homozygous mice (RXRγ$^{-/-}$) were produced from heterozygous matings, which followed expected Mendelian inheritance patterns.

RNA analysis.

To verify that the RNAs encoding the RXRγ proteins were disrupted by the methods described in Example 1, an RNAse protection assay was performed. Total RNAs were prepared from limb muscle, heart and brain tissues of 2 month-old mice using the isothiocyanate-phenol technique (Chomczynski, P. & Sacchi, N., *Anal. Biochem.* 162:156–159 (1987)). Poly(A)+ RNA was prepared using a commercially available RNA purification kit (Pharmacia, Piscataway, N.J.). RT-PCR reactions were carried out as described (Bouillet, P., et al., *Dev. Biol.* 170:420–433 (1995)) in a buffer containing 10 mM Tris-HCl, pH 8.8, 50 mM KCl, 1.5 MM MgCl$_2$ and 0.2 μg BSA with 1 μg of RNA in a final volume 50 μl. The following primer oligonucleotides were used:

P1 (5'-GCTCCCCTGGTCACACTGGCTCG-3') (SEQ ID NO:1);

P2 (5'-TTGGGCTCCGGAACCACGCG-3') (SEQ ID NO:2); and

P3 (5'-GTTCCACAGCAAGTTCGGC-3') (SEQ ID NO:3).

These primers were specific to exons E2, E1B and E5, respectively (FIG. 2). After 35 cycles, the reaction products were analyzed on 2% agarose gels.

For Northern blotting, 3 μg of poly(A)+ RNA was fractionated on a formaldehyde agarose gel. Filters hybridized with a RXRγ fill length cDNA probe were washed at 65° C. for 30 min. in 0.2×SSC, 0.1% SDS. For RNAse protection analysis, 50 μg of RNA was used per hybridization reaction. Preparation of probes and hybridization were performed as previously described (Ausubel, F. M., et al., "*Current Protocols in Molecular Biology*", Green Pub. Assoc. and Wiley-Interscience, Wiley, N.Y. (1987)). To prepare the RXRα riboprobe, a cDNA fragment corresponding to nucleotides 81 to 675 (numbering according to Genbank sequence number M84817) was subcloned into the EcoRI site of pBluescript SK (–) (a gift of J. Broccard) and the probe was synthesized with T7 RNA polymerase using BamHI-linearized template. The RXRβ antisense riboprobe was transcribed from a cDNA template corresponding to nucleotides 93 to 1437 (numbering according to Genbank sequence number M84817) subcloned into the EcoRI and HindIII sites of pBluescript SK (–) and linearized with BamHI (at nucleotide position 890) prior to transcription.

Immunocytochemistry.

Frozen, 10 μm thick sections were collected on poly-L-lysine coated slides and fixed for 15 minutes in Zamboni fixative. This step was followed by treatment with 1% H$_2$O$_2$ in order to block endogenous peroxidase. Staining with the anti-RXRγ antibody was as described (Sugawara, A., et al., *Endocrinol.* 136:1766–1733 (1995)). The sections were counterstained with 1% methylene green.

Biochemical and electrophysiological analyses.

The biochemical analysis of free thyroxine, triiodothyronine, glucose, triglycerides, myoglobin, creatine as well as creatine kinase levels, were performed using procedures routinely applied in human diagnostics. The electrophysiological tests on muscles were performed as described (Kennel, P. F., et al.,, Neurobiol. Dis., 3:137–37 (199).

Results

Expression of RXRγ in mutant mice.

As described in Example 1, heterozygous (RXRγ$^{+/-}$) chimeric animals derived from the YJ3 and YJ36 clones demonstrated germline transmission of the RXRγ transgene. For each of these lines, homozygous mice (RXRγ$^{-/-}$) were produced from heterozygous matings. Southern analysis with probe B, corresponding to the deleted region (see FIG. 2), failed to detect any hybridizing fragment in the DNA from RXRγ$^{-/-}$ mice (FIG. 4), demonstrating the absence of the sequences encoding the DNA-binding domain in the mutant genome. In addition, immunohistological analysis with an anti-RXRγ1 antibody (Sugawara, A., et al., Endocrinol. 136:1766–1733 (1995)) revealed clear labeling of a subset of muscle nuclei in wild type (WT), but not in mutant embryos (FIG. 5).

Figure 6:
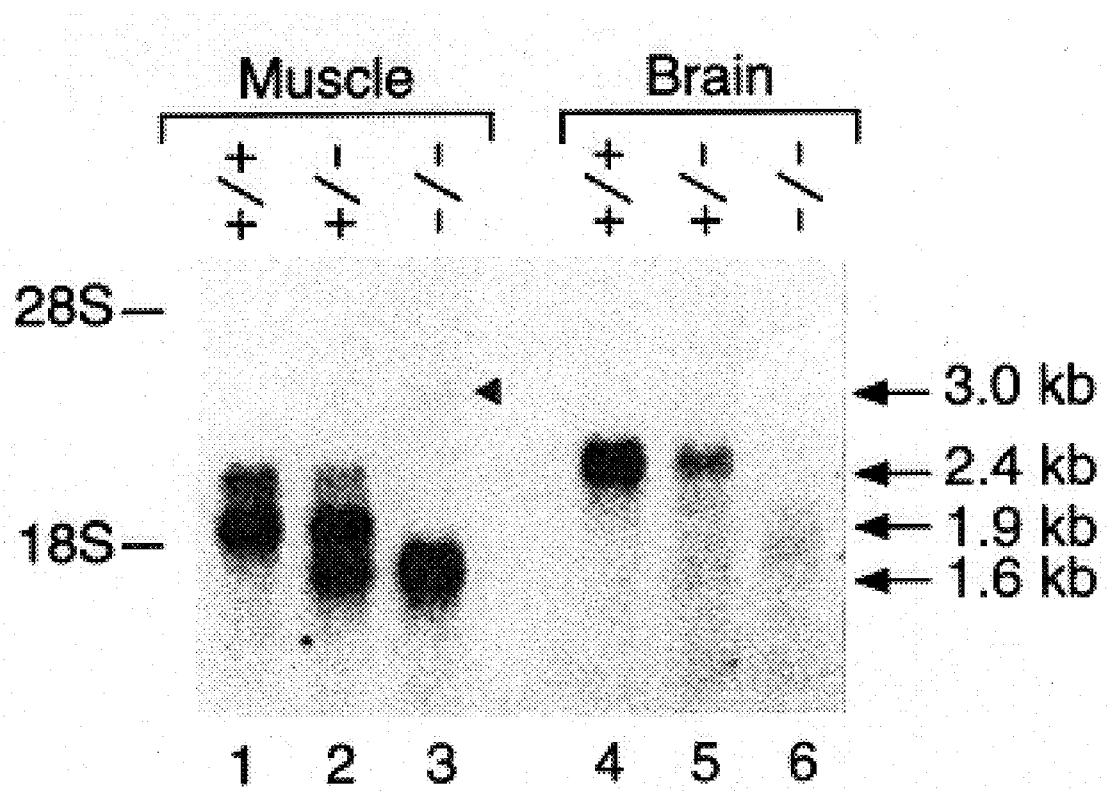
FIG. 6. Transcript analysis in RXRγ mutants. Muscle and brain poly (A)+ RNAs prepared from adult tissues of wild type (+/+), heterozygote (+/−) or mutant (−/−) mice, were analyzed by Northern blot with a RXRγ full length cDNA probe. The presence of equal amounts of RNA in each lane was confirmed by hybridization with a RXRα cDNA probe (data not shown). The arrowhead points to a minor 3 kb transcript present in RXRγ$^{-/-}$ muscle tissue.
Figure 7:
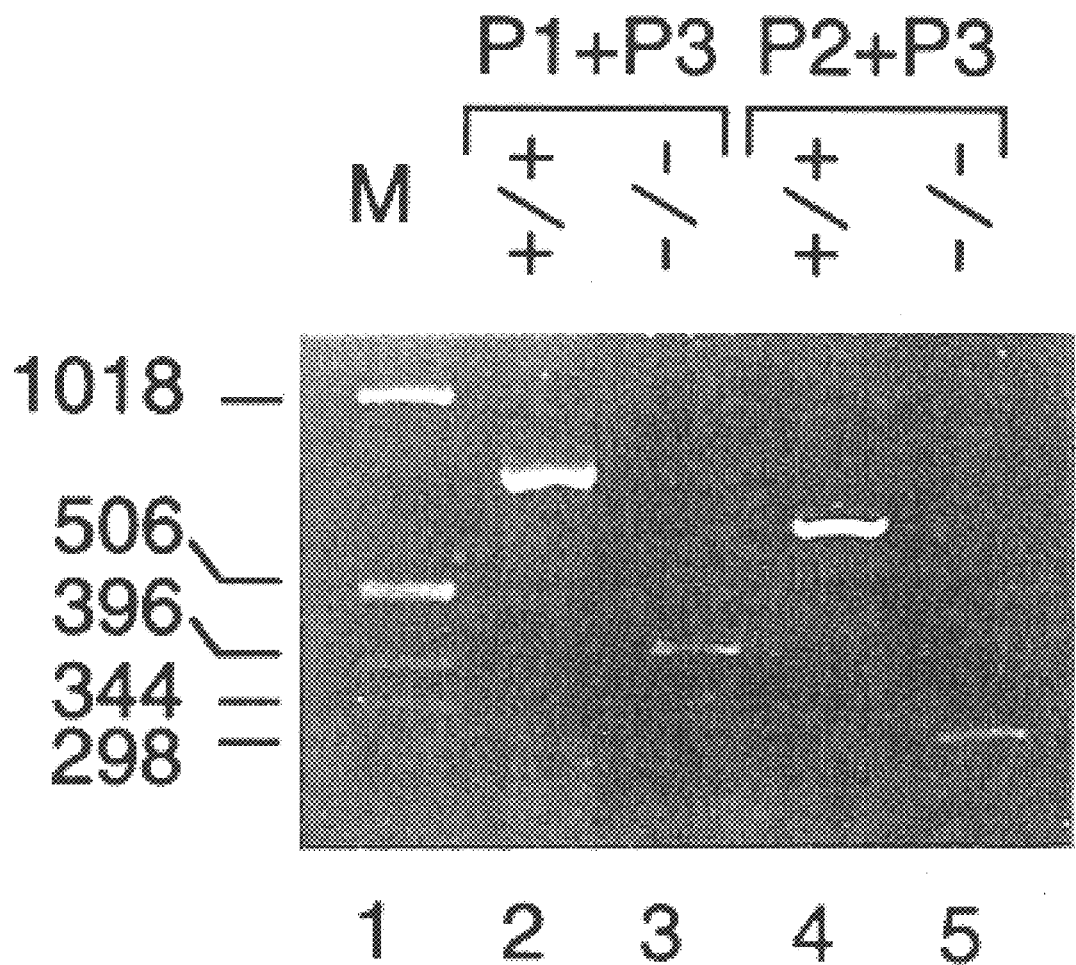
FIG. 7. Transcript analysis in RXRγ mutants. Detection of RXRγ1 (primers P1 (SEQ ID NO:1) and P3(SEQ ID NO:3)) and RXRγ2 (primers P2 (SEQ ID NO:2) and P3) isoform transcripts by RT-PCR in wild type(+/+) and mutant (−/−) muscle total RNA. Sequencing of the amplification products revealed that the fragments in lanes 2 and 4 correspond to wild type transcripts, while fragments visualized in lanes 3 and 5 represent, respectively, RXRγ1 and RXRγ2- related transcripts resulting from splicing of exons E2 to E5 and E1B to E5 (see FIG. 2).

To determine which polypeptides might possibly originate from the mutant locus, adult muscle and brain RNA was analyzed by Northern Blot with a full length RXRγ cDNA probe. RXRγ transcripts were no longer detected in mutant brain, whereas new 1.6 kb and 3 kb transcripts appeared to be generated from the mutant allele in muscle (FIG. 6). The major 1.6 kb mutant RNA species is likely to correspond to RXRγ2-related transcripts, in which E1B is spliced to E5, since: (i) its size corresponds to a 300-nucleotide deletion (the combined length of E3 and E4) from the normal 1.9 kb RXRγ2 transcript and transcripts in which E1B is spliced to E5 were readily detected in mutant muscle by RT-PCR (FIG. 7, lane 5); and (ii) it is unlikely to correspond to RXRγ1-related transcripts (E2 spliced to E5) which would be larger in size and which are not detectable by Northern blot in brain where RXRγ1 is normally the only RXRγ isoform present. This 1.6 kb transcript conceptually encodes a polypeptide initiated from the first methionine in the 5th exon and consisting essentially of an isolated ligand-binding domain. It is unknown whether such a protein is actually made, as a suitable antibody allowing such a determination is presently unavailable. The nature of the second novel 3 kb transcript is presently unclear, but its absence in brain suggests that it may also be initiated from the RXRγ2 promoter and may result from the use of cryptic splice sites located in intronic or NEO sequences. In addition to these transcripts which are readily detectable by Northern blot, RT-PCR analysis also revealed the presence of RXRγ1-related transcripts, both in mutant brain and muscle, in which exon E2 is spliced to exon E5 (FIG. 7 and data not shown). These latter transcripts, in which the 3' RXRγ sequence (downstream of exon 5) is out of frame with 5 upstream sequence, are unlikely to encode any functional polypeptide. In any event, the transactivator function of RXRγ is abrogated in the mutants, as all the above possible RXRγ-derived polypeptides lack the DNA-binding domain. In addition, since the mutation did not result in any abnormal dominant phenotype, it is unlikely that the putative protein encoded by the 1.6 kb transcript exerts any drastic deleterious dominant negative effect. Thus the present RXRγ mutation is most probably a null mutation.

Analysis of RXRγ null mutant mice.

Viable homozygous mutant mice were obtained from heterozygous crosses at the expected Mendelian frequencies (out of 408 animals, 97 mice were WT, 212 were RXRγ$^{+/-}$ and 99 were RXRγ$^{-/-}$). Irrespective of their genetic background, RXRγ$^{+/-}$ mice were indistinguishable from their RXRγ$^{+-}$ or WT littermates with respect to growth, fertility, viability and apparent behavior in the animal facility. In addition, analysis of serial histological sections and of whole mount skeletal preparations of 18.5 dpc mutant fetuses did not reveal any abnormalities (not shown). As RXRγ is expressed in pituitary thyrotrope cells (Sugawara, A., et al., Endocrinol. 136:1766–1733 (1995)) and the thyroid gland (Dollé, P., et al, Mech. Dev. 45:91–104 (1994)), it was investigated whether thyroid hormone homeostasis was affected by measuring the serum levels of free thyroxine and triiodothyronine. No differences in the levels of either of these thyroid hormones were detected between mutant and WT mice (data not shown). General metabolic tests (for glucose, triglycerides, myoglobin, creatine and creatine kinase) also failed to reveal any abnormalities in RXRγ mutant mice (not shown).

The function of skeletal muscles in mutant mice was tested by electromyography, as these muscles correspond to one of the major sites of RXRγ expression (Dollé, P., et al., Mech. Dev. 45:91–104 (1994)). Upon electric stimulation (12.8 mA) of the sciatic nerve, the response of the gastrocnemius caput muscle was identical in RXRγ$^{-/-}$ and WT animals with respect to amplitude, duration and number of motor units (data not shown).

Figure 8:
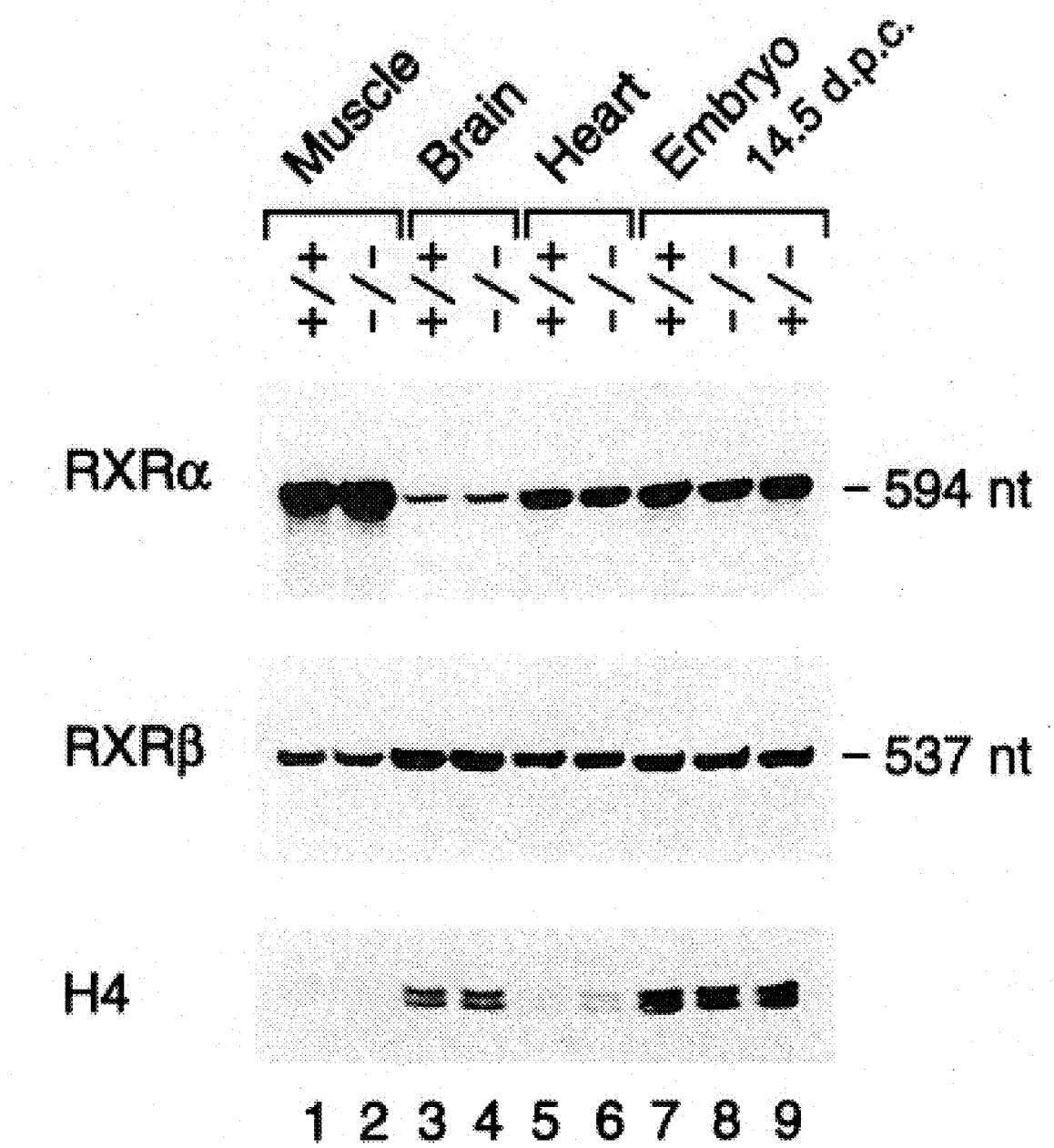
FIG. 8. Determination of RXRα and RXRβ transcripts levels in RXRγ mutants. RNAs from 14.5 dpc fetuses or adult tissues from WT (+/+), heterozygous (+/−) and homozygous (−/−) mutant animals were analyzed by an RNAase protection assay using RXRα- and RXRβ-specific antisense riboprobes. Hybridization with a histone H4 antisense riboprobe was used as an internal control to evaluate the amounts of RNA in each lane (bottom).

To test whether the lack of any apparent defect in RXRγ$^{-/-}$ mutants could result from compensatory increases in the expression levels of the remaining RXRs, RXRα and RXRβ mRNAs were quantified by RNase protection in adult muscle, heart and brain as well as in whole 14.5 dpc fetuses. No differences were detected between mutant and WT tissues (FIG. 8), therefore excluding this hypothesis.

Example 3

Compound RXRγ/RXRα and/or RXRγ/RXRβ Mutant Mice

Experimental Procedures

Production of compound mutant animals.

RXRγ null mutants were produced from intercrosses of RXRγ$^{+/-}$ mice that were raised on pure (129/SV) or mixed genetic background (129/SVxC57BL/6). The double RXRγ/RXRβ mutants were obtained from the intercrosses of RXRγ$^{-/-}$/RXRβ$^{+/-}$, while RXRγ$^{-/-}$/RXRα$^{-/-}$ mutants were derived from RXRγ$^{-/-}$/RXRα$^{+/-}$ intercrosses. The triple RXRγ$^{-/-}$/RXRβ$^{-/-/RxRα+/-}$ animals were produced from matings of RXRγ$^{-/-}$/RXRβ$^{-/-}$/RXRα$^{+/-}$ males with RXRγ$^{-/-}$/RXRβ$^{-/-}$ or RXRγ$^{-/-}$/RXRβ$^{-/-}$ females. RXRγ$^{-/-}$ genotypes were determined with probe C on KpnI-BamHI digested DNA (FIGS. 2, 3), while RXRα and RXRβ genotyping were as described (Kastner, P., et al., Cell 78:987–1003 (1994); Kaster, P., et al., Genes & Dev. 10:80–92 (1996)).

Analysis of compound mutant animals.

Biochemical and electrophysiological analyses of compound mutant mice were performed as described in Example 2. Growth deficiencies were determined by weighing mice on standard laboratory scales, and weights expressed as a ratio of that of RXRγ$^{-/-}$/RXRβ$^{+/-}$ or RXRγ$^{-/-}$ littermates. Histological and skeletal defects were determined as disclosed in WO 94/26100.

Results

To investigate whether important functions of RXRγ could be masked by the presence of other RXRs, the RXRγ null mutation was introduced on RXRα and/or RXRβ mutant genetic backgrounds. Using these methods, viable double RXRγ$^{-/-}$/RXRβ$^{-/-}$, as well as triple RXRγ$^{-/-}$/

Figure 9:
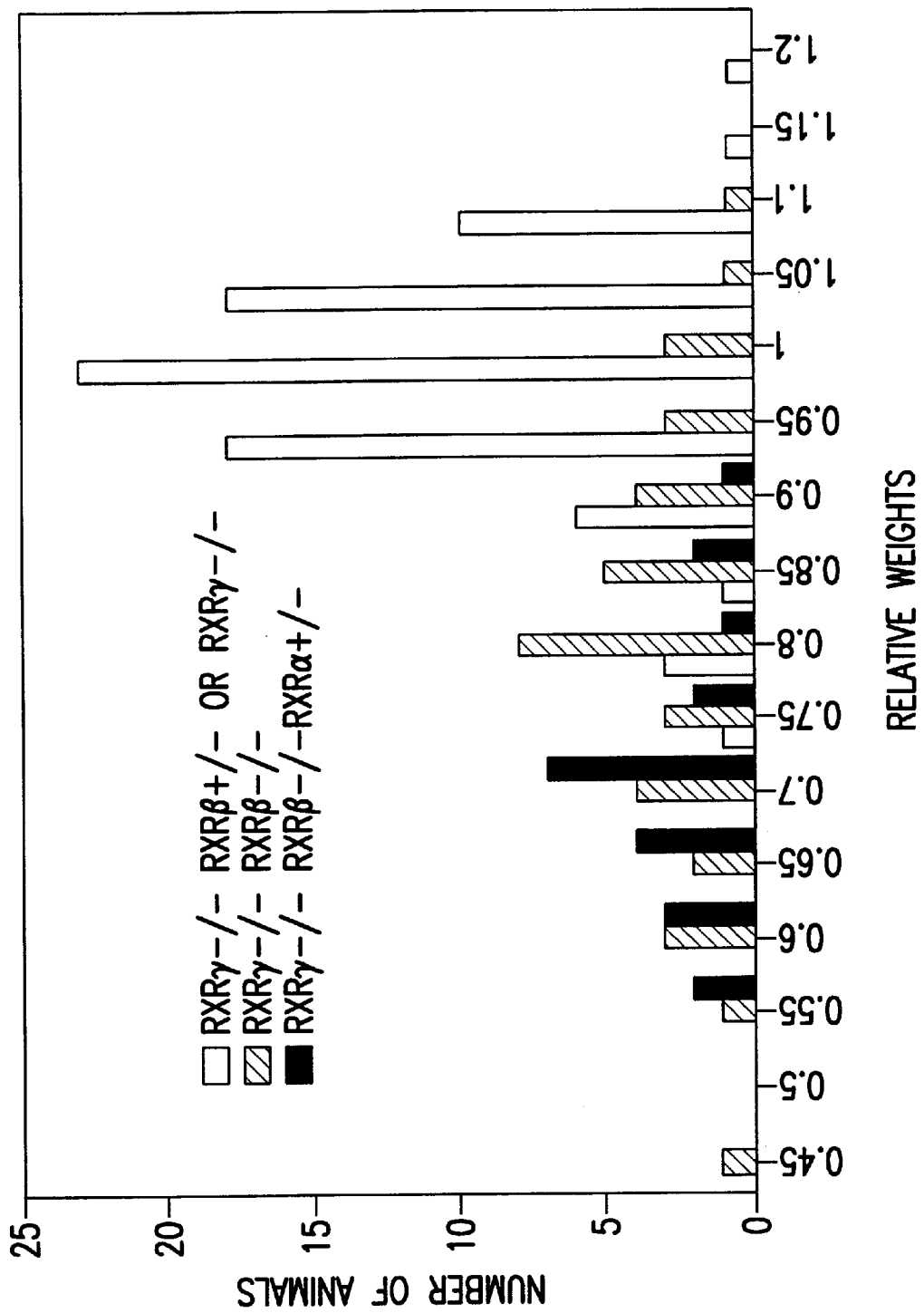
FIG. 9. Weight distribution of control and mutant animals. Weights of 2–3-week-old RXRγ$^{-/-}$/RXRβ$^{+/-}$ or RXRγ$^{-/-}$, RXRγ$^{-/-}$/RXRβ$^{-/-}$ and RXRγ$^{-/-}$/RXRβ$^{-/-}$/RXRα$^{+/-}$ animals are represented as ratios relative to the average weight of their RXRγ$^{-/-}$/RXRβ$^{+/-}$ or RXRγ$^{-/-}$ littermates.

RXRβ$^{-/-}$RXRα$^{+/-}$ mutants were readily obtained. These mutants displayed a marked growth deficiency relative to their RXRγ$^{-/-}$/RXRβ$^{+/-}$ or RXRγ$^{-/-}$ littermates whose growth was similar to that of WT animals (approximately 20% weight deficit, see FIG. 9). All of the live-born RXRγ$^{-/-}$ RXRβ$^{-/-}$/RXRα$^{+/-}$ mutants have reached adult age to date, indicating that a single. RXRα allele is sufficient to carry out all of the vital developmental and postnatal functions of the RXR family of receptors, particularly all of the developmental functions which depend on RARs and may require RXR partnership (Dollé, P., et al., Mech. Dev. 45:91–104 (1994); Kastner, P., et al., Cell 83:859–869 (1995)). In addition, when RXRγ$^{-/-}$/RXRα$^{-/-}$ mutants were examined at 14.5 dpc, they exhibited the same cardiac and ocular defects previously found in RXRα null mutants and no additional abnormalities could be observed in these fetuses after analysis of serial histological sections. In particular, no obvious defect could be detected in the morphology of skeletal muscles (data not shown).

General Discussion

The present results show that RXRγ is dispensable for embryonic development and postnatal life in the mouse, even though it exhibits a highly tissue-specific expression pattern in the developing embryo (e.g., all skeletal muscle precursors) and in the adult mouse (Mangelsdorf, D. J., et al., Genes & Dev. 6:329–344 (1992); Dollé, P., et al., Mech. Dev. 45:91–104 (1994); Nagata, T., et al., Gene 142:183–189 (1994); Nagata, T., et al., Gene 142:183–189 (1994)). Moreover, the function of RXRγ was not revealed when the RXRγ mutation was introduced into RXRα- and/or RXRβ-mutated genetic backgrounds. However, given the evolutionary conservation of RXRγ across vertebrates, it is clear that RXRγ must perform (a) function(s) conferring a selective advantage. In this respect, it is puzzling that RXRγ, even though conserved at the sequence level, is apparently expressed in different structures in mouse and chicken embryos (neural crest derivatives in chicken (Rowe, A., et al., Develop. 111:771–778 (1991)) and myogenic lineage in mouse). Thus some specific function(s) of RXRγ in the mouse may have evolved rather recently and might be involved in the "fine-tuning" of the functioning of certain tissues, rather than in the control of major developmental and/or physiological events. In this respect, possible defects might become apparent in RXRγ$^{-/-}$ mice exposed to a less-protected environment than the present laboratory conditions.

The role of RXRs is expected to be pleiotropic, since besides their capacity to homodimerize, they are thought to be heterodimeric partners for at least 18 distinct nuclear receptors (for review, see Mangelsdorf, D. J., and Evans, R. M., Cell 83:841–850 (1995)). Among these partners, knock-out studies have demonstrated the involvement of RARs in a vast array of developmental functions (Lohnes, D., et al., Development 120:2723–2748 (1994); Mendelsohn, C., Develop. 120:2749–2771 (1994); Luo, J., et al., Mech. Develop. 55:33–44 (1996)) and other studies have linked thyroid hormone receptors, vitamin D3 receptor and peroxisomal proliferator-activated receptor γ to major physiological processes (De Groot, L., et al., Endocrinology, W.B. Sanders Co., pp. 507–900 (1995); Hughes, M., et al., Science 242:1702–1705 (1988); Tontonoz, P., et al., Curr. Opin. Genet. Dev. 5:571–576 (1995)). Moreover, the synergy observed between RXRα and RAR mutations (Kastner, P., et al., Cell 78:987–1003 (1994); Kastner, P., et al., Cell 83:859–869 (1995)) supports the idea that heterodimerization with RXR does occur in vivo. Therefore mutations of RXRs, including those of RXRγ, should ultimately reproduce the defects associated with inactivations of their heterodimeric partners, in particular the spectrum of developmental abnormalities found in RAR double mutants. It is thus surprising that the double RXRγ$^{-/-}$/RXRβ$^{-/-}$, as well as the triple RXRγ$^{-/-}$/RXRβ$^{-/-}$/RXRα$^{+/-}$ mutants were essentially normal, displaying no obvious congenital or postnatal abnormalities besides a marked growth deficiency and, due to loss of RXRβ, male sterility (Kastner, P., et al., Genes. Dev. 10:80–92 (1996)). It is thus apparent that a single allele of RXRα can perform most of the developmental functions of the RXR family of receptors. On the other hand, the present observation that RXRα$^{-/-}$/RXRγ$^{-/-}$ double mutant embryos are not more affected than are single RXRα$^{-/-}$ mutants also clearly shows that RXRβ alone can perform some of these functions. Therefore, the fact that RXRα alone and, to a certain extent RXRβ alone, are sufficient for the completion of a number of developmental RXR functions, clearly indicates the existence of a large degree of functional redundancy amongst RXRs. In this respect, the RXR situation is different from that of RARs, since all of types of RAR double mutants displayed much broader sets of defects than single mutants (Rowe, A., et al, Develop. 111:771–778 (1991); Lohnes, D., et al, Develop. 120:2723–2748 (1994); Mendelsohn, C., Develop. 120:2749–2771 (1994)).

Since the function of RXRs is likely to be exerted through heterodimers, the function of RXRγ may become apparent only upon concomitant mutation of its partners, as shown previously in the case of mutations affecting RXRα together with either RARα or RARγ (Kastner, P., et al., Cell 78:987–1003 (1994); Kastner, P., et al., Cell 83:859–869 (1995)). Of particular interest will be the combinations of mutations affecting RXRγ together with either mutations of RARβ, thyroid hormone receptor a or thyroid hormone receptor β, since these genes are coexpressed with RXRγ in a number of tissues (Dollé, P., et al., Mech. Dev. 45:91–104 (1994); Bradley, D., et al., Proc. Natl. Sci. USA 86:7250–7254 (1989)).

The disclosure of all references, patent applications and patents recited herein are hereby incorporated by reference in their entirety.

What is claimed is:

1. A mouse whose germ cells and somatic cells contain an insertion of an exogenous DNA within the gene loci of exons 3 and 4, such that said insertion causes said mouse to be deficient in the normal expression of a RXRγ, wherein said gene loci comprises the entire DNA-binding domain of an endogenous retinoid X receptor-γ (RXRγ) gene.

2. The mouse of claim 1, herein said exogenous DNA comprises a selectable marker gene.

3. The mouse of claim 1, wherein said gene loci further comprises B region of said RXRγ gene.

4. The mouse of claim 1, wherein said insertion causes said mouse to be homozygous for a deficiency in the normal expression of said RXRγ.

5. The mouse of claim 1, wherein said insertion causes said mouse to be heterozygous for a deficiency in the normal expression of said RXRγ.

6. A mammalian cell line which contains an insertion of an exogenous DNA within the gene loci of exons 3 and 4, such that said insertion causes said cell line to be deficient in the normal expression of a RXRγ, wherein said gene loci comprises the entire DNA-binding domain of an endogenous retinoid X receptor-γ (RXRα) gene.

7. The cell line of claim 6, wherein said cell line is a pluripotent mouse cell line.

8. The cell line of claim 6, wherein said insertion causes said cell line to be homozygous for a deficiency in the normal expression of said RXRγ.

9. The cell line of claim 6, wherein said insertion causes said cell line to be heterozygous for a deficiency in the normal expression of said RXRγ.

10. A method of identifying an agent which is an antagonist or agonist of a retinoid X receptor-γ (RXRγ), comprising the steps of:

(a) incubating said agent with the mouse of claim 1, (b) determining the effect said agent has on the development of said mice (a); and (c) comparing said effect of said agent on said mice (a) to the effect of said agent on a mouse without said insertion and exhibiting normal expression of a RXRγ.

11. The method of claim 10, wherein said mouse (a) contain an inserted DNA comprising a RXRγ response element operably linked to a marker gene.

12. A method of identifying an agent which is an antagonist or agonist of a retinoid X receptor-γ (RXRγ), comprising the steps of:

(a) incubating said agent with the cell line of claim 6;

(b) determining the amount of said agent bound by said cell line (a); and (c) comparing said amount of agent bound by said cell line (a) to the amount of agent bound by a cell line without said insertion and exhibiting normal expression of a RXRγ.

13. The method of claim 12, wherein said cell line (a) contain an inserted DNA comprising a RXRγ response element operably linked to a marker gene.

* * * * *

UNITED STATES PATENT AND TRADEMARK OFFICE
CERTIFICATE OF CORRECTION

PATENT NO. : 6,093,873
DATED : July 25, 2000
INVENTOR(S) : Chambon et al.

It is certified that error appears in the above-identified patent and that said Letters Patent is hereby corrected as shown below:

Title page, Item [54], and Column 1, line 3,
After "RXR" insert -- A GAMMA --.

Column 12,
Line 25, delete "1.5 MM MgCl$_2$" and insert therein --1.5 mM MgCl$_2$ --.
Line 54, delete "M84817" and insert therein -- M84818 --.

Column 13,
Line 5, delete "(199)" and insert therein -- (1996) --.

Column 14,
Line 45, delete "RXRγ$^{-/-}$/RXRβ$^{-/-}$/RxRα+/-" and insert therein -- RXRγ$^{-/-}$/RXRβ$^{-/-}$/RxRα$^{+/-}$ --.

Column 16,
Line 48, delete "a" and insert therein -- α --.

Column 17, claim 1,
Line 39, after the term "A" and before the term "mouse" insert -- transgenic --.
Line 43, delete "comprises" and insert therein -- comprise --.

Column 17, claim 2,
Line 45, delete "herein" and insert therein -- wherein --.

Column 17, claim 3,
Line 48, delete "comprises" and insert therein -- comprise --.

Column 17, claim 6,
Line 58, delete "comprises" and insert therein -- comprise --.
Line 59, delete "(RXRα)" and insert therein -- (RXRγ) --.

Column 18, claim 10,
Lines 45 and 46, delete "mice" and insert therein -- mouse --.

Column 18, claim 11,
Line 50, delete "contain" and insert therein -- contains --.

UNITED STATES PATENT AND TRADEMARK OFFICE
CERTIFICATE OF CORRECTION

PATENT NO. : 6,093,873
DATED : July 25, 2000
INVENTOR(S) : Chambon et al.

It is certified that error appears in the above-identified patent and that said Letters Patent is hereby corrected as shown below:

Column 18, claim 13,
Line 64, delete "contain" and insert therein -- contains --.

Signed and Sealed this

Ninth Day of April, 2002

Attest:

*Attesting Officer*

JAMES E. ROGAN
*Director of the United States Patent and Trademark Office*

SEQUENCE LISTING (1) GENERAL INFORMATION:

(iii) NUMBER OF SEQUENCES: 3

(2) INFORMATION FOR SEQ ID NO:1:

-continued

```
    (i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:1:

GCTCCCCTGG TCACACTGGC TCG                                       23

(2) INFORMATION FOR SEQ ID NO:2:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:2:

TTGGGCTCCG GAACCACGCG                                           20

(2) INFORMATION FOR SEQ ID NO:3:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:3:

GTTCCACAGC AAGTTCGGC                                            19
```